(12) United States Patent
Mehta et al.

(10) Patent No.: US 7,501,443 B2
(45) Date of Patent: Mar. 10, 2009

(54) FLAVAXATE DERIVATIVES AS MUSCARINIC RECEPTOR ANTAGONISTS

(75) Inventors: Anita Mehta, Plainfield, IL (US); Sanjay Kumar Srivastava, Haryana (IN); Jang Bahadur Gupta, Dusseldorf (DE)

(73) Assignee: Ranbaxy Laboratories Limited, Gurgaon (IN)

( * ) Notice: Subject to any disclaimer, the term of this patent is extended or adjusted under 35 U.S.C. 154(b) by 123 days.

(21) Appl. No.: 10/540,062

(22) PCT Filed: Dec. 23, 2002

(86) PCT No.: PCT/IB02/05591

§ 371 (c)(1),
(2), (4) Date: Jan. 21, 2006

(87) PCT Pub. No.: WO2004/056811

PCT Pub. Date: Jul. 8, 2004

(65) Prior Publication Data

US 2006/0128781 A1  Jun. 15, 2006

(51) Int. Cl.
*A61K 31/46* (2006.01)
*C07D 211/18* (2006.01)

(52) U.S. Cl. .................................. 514/337; 546/283.1

(58) Field of Classification Search ................. 514/337; 546/283.1
See application file for complete search history.

(56) References Cited

U.S. PATENT DOCUMENTS

| 3,176,019 | A | 3/1965 | Campbell et al. | ........ 260/293.4 |
| 5,281,601 | A | 1/1994 | Cross et al. | ................ 514/320 |
| 5,948,792 | A | 9/1999 | Tsuchiya et al. | ........... 514/317 |
| 6,130,232 | A | 10/2000 | Mase et al. | ................. 514/318 |
| 6,174,900 | B1 | 1/2001 | Okada et al. | ................ 514/317 |

FOREIGN PATENT DOCUMENTS

| EP | 0 072 620 | 2/1983 |
| EP | 0 108 986 | 5/1984 |
| EP | 0 267 319 | 5/1988 |
| EP | 0 325 571 | 7/1989 |
| EP | 0 388 054 | 9/1990 |
| EP | 0 801 067 | 10/1997 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16018 | 8/1993 |
| WO | WO 93/16048 | 8/1993 |
| WO | WO 96/33973 | 10/1996 |
| WO | WO 97/45414 | 12/1997 |
| WO | WO 98/05641 | 2/1998 |
| WO | WO 98/29402 | 7/1998 |

OTHER PUBLICATIONS

King, Med. Chem. Principle and Practice (1994), pp. 206-208.*
Kubo et al., "Cloning sequencing and expression of complementary DNA encoding the muscarinic acetylcholine receptor", *Nature*, 323(2):411-416 (1986).

Bonner et al., "Identification of a Family of Muscarinic Acetylcholine Receptor Genes", *Science*, 237:527-531 (1987).
Eglen et al., "Muscarinic receptor ligands and their theraputic potential", *Current Opinion in Chemical Biology*, 3:426-432 (1999).
Eglen et al., "Theraputic opportunities from muscarinic receptor research", *Trends in Pharmacological Sciences*, 22(8):409-414 (2001).
Felder et al., "Theraputic Opportunities for Muscarinic Receptors in the Central Nervous System", *Journal of Medicinal Chemistry*, 43(23):4333-4353 (2000).
Broadley and Kelly, "Muscarinic Receptor Agonists and Antagonists", *Molecules*, 6:142-193 (2001).
Birdsall et al., "Muscarinic receptors: it's a knockout", *Trends in Pharmacological Sciences*, 22(5):215-219 (2001).
de Groat and Yoshimura, "Pharmacology of the Lower Urinary Tract", *Annual Review of Pharmacology and Toxicology*, 41:691-721 (2001).
Steers, "The future direction of neuro-urology drug research", *Current Opinion in CPNS Investigational Drugs*, 2(3):268-282, (2000).
Chapple, "Muscarinic receptor antagonists in the treatment of overactive bladder", *Urology*, 55(Suppl. 5A):33-46 (2000).
Steers, Barrot, Wein, "Voiding dysfunction: diagnosis classification and management", in: *Adult and Pediatric Urology*, ed. Gillenwater, Grayhack, Howards, Duckett. Mosby, St. Louis, MO; 1220-1325, 3rd edition (1996).
Sagara et al., "Cyclohexylmethylpiperidinyltriphenylpropioamide: A Selective Muscarinic $M_3$ Antagonist Discriminating against the Other Receptor Subtypes", *Journal of Medicinal Chemistry*, 45:984-987 (2002).
Braish et al., "Construction of the $(1\alpha,5\alpha,6\alpha)$-6-Amino-3-azabicyclo[3.1.0]hexane Ring System", *Synlett*, 1100-1102 (1996).
Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).
Chen and Prusoff, "Relationship between the inhibition constant ($K_1$) and the concentration of inhibitor which causes 50 per cent inhibition ($I_{50}$) of an enzymatic reaction", *Biochemical Pharmacology*, 22:3099-3108 (1973).
* cited by examiner

*Primary Examiner*—Taofiq A Solola
(74) *Attorney, Agent, or Firm*—Jayadeep R. Deshmukh, Esq; George E. Heibel, Esq.

(57) ABSTRACT

This invention generally relates to the derivatives of 3.6-disubstituted azabicyclo [3.1.0] hexanes of the following formula [IA]. The compounds of this invention can function as muscarinic receptor antagonists, and can be used for the treatment of various diseases of the respiratory, urinary and gastrointestinal systems mediated through muscarinic receptors. The invention also relates to a process for the preparation of the compounds of the present invention, pharmaceutical compositions containing the compounds of the present invention and the :hl ethods for treating the diseases mediated through muscarinic receptors.

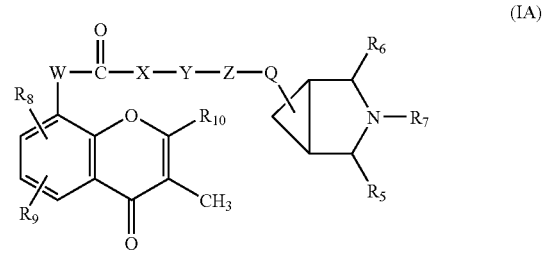

(IA)

4 Claims, No Drawings

FLAVAXATE DERIVATIVES AS MUSCARINIC RECEPTOR ANTAGONISTS

FIELD OF THE INVENTION

This invention generally relates to the derivatives of 3,6-disubstituted azabicyclo[3.1.0] hexanes.

The compounds of this invention can function as muscarinic receptor antagonists, and can be used for the treatment of various diseases of the respiratory, urinary and gastrointestinal systems mediated through muscarinic receptors.

The invention also relates to a process for the preparation of the compounds of the present invention, pharmaceutical compositions containing the compounds of the present invention and the methods for treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; Science, 1987; 237: 527).

A review in *Current Opinions in Chemical Biology* 1999; 3: 426, as well as in *Trends in Pharmacological Sciences*, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in *J. Med. Chem.*, 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in *Molecules*, 2001, 6: 142.

N. J. M. Birdsall et. al. in *Trends in Pharmacological Sciences*, 2001; 22:215 have also summarized the recent developments on the role of different muscarinic receptor subtypes using different muscaranic receptors of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of *Pharmacological Toxicol.*, 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in *Curr. Opin. Invest. Drugs*, 2: 268, C. R. Chapple et. al. in *Urology*, 55: 33), Steers W D, Barrot D M, Wein A J, 1996, Voiding dysfunction: diagnosis classification and management. In "Adult and Pediatric Urology," ed. J Y Gillenwatter, J T Grayhack, S S Howards, J W Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. Nos. 5,281,601. 6,174,900, 6,130,232 and 5,948,792; WO 97/45414 are related to 1,4disubstituted piperidine derivatives; WO 98/05641 describes fluorinated, 1,4-disubstitued piperidine derivatives; WO 93/16018 and WO96/33973 are other close art references.

A report in *J. Med. Chem.*, 2002; 44:984, describes cyclohexylmethyl piperidinyl triphenylpropioamide derivatives as selective $M_3$ antagonist discriminating against the other receptor subtypes.

SUMMARY OF THE INVENTION

The present invention provides 3,6-disubstituted azabicyclo[3.1.0]hexanes which function as muscarinic receptor antagonists which are useful as safe treatment of various diseases of the respiratory, urinary and gastrointestinal systems, and method for the synthesis of the compounds.

The invention also provides pharmaceutical compositions containing the compounds, and which may also contain acceptable carriers, excipients or diluents which are useful for the treatment of various diseases of respiratory, urinary and gastrointestinal systems.

The invention also includes the enantiomers, diastereomers, polymorphs, pharmaceutically acceptable salts, pharmaceutically acceptable solvates, esters, N-oxides and metabolites of these compounds having the same type of activity.

The invention further includes pharmaceutical compositions comprising the compounds of the present invention, their enantiomers, diastereomers, polymorphs, pharmaceutically acceptable solvates, esters, N-oxides or metabolites, in combination with pharmaceutically acceptable carrier and optionally included excipients.

Other advantages of the invention will be set forth in the description which follows and in part will be apparent from the description or may be learnt by the practice of the invention. The objects and the advantages of the invention may be realized and obtained by means of the mechanisms and combinations pointed out in the appended claims.

In accordance with one aspect of the present invention, there is provided a compound having the structure of Formula I:

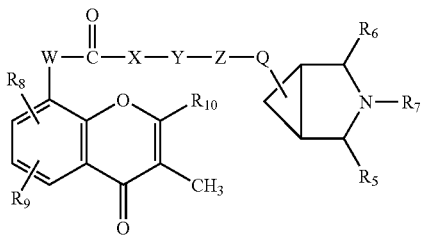

Formula I and its pharmaceutically acceptable salts, pharmaceutically acceptable solvates, esters, enantiomers, diastereomers, N-oxides, polymorphs or metabolites, wherein W represents $(CH_2)_p$, where p represents 0 to 1;

X represents an oxygen, sulphur, —NR or no atom, wherein R represents hydrogen or $C_{1-6}$ alkyl;

Y represents $CHR_1CO$, wherein $R_1$ represents hydrogen, methyl or $(CH_2)_q$ wherein q represents 0 to 4;

Z represents oxygen, sulphur, $NR_2$, wherein $R_2$ represents hydrogen, or $C_{1-6}$ alkyl;

Q represents $(CH_2)_n$, wherein n represents 0 to 4, or $CHR_3$ wherein $R_3$ represents H, OH, $C_{1-6}$ alky, $C_{1-6}$ alkenyl, $C_{1-6}$ alkoxy or $CH_2CHR_4$ wherein $R_4$ represents H, OH, lower alkyl ($C_1$-$C_4$) or lower alkoxy ($C_1$-$C_4$);

$R_5$ and $R_6$ are independently selected from H, COOH, $CH_3$, $CONH_2$, $NH_2$, $CH_2NH_2$;

$R_7$ represents hydrogen, $C_1$-$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, hetero arylalkenyl group may be substituted with lower alkyl ($C_1$-$C_4$), lower perhalo alkyl ($C_1$-$C_4$), cyano, hydroxyl, nitro, lower alkoxycarbonyl, halogen, lower alkoxy ($C_1$-$C_4$), lower perhaloalkoxy ($C_1$-$C_4$), unsubstituted amino, N-lower alkylamino ($C_1$-$C_4$), N-lower alkylamino carbonyl ($C_1$-$C_4$) N,N-lower dialkylamino ($C_1$-$C_4$), N,N-lower dialkylaminocarbonyl;

$R_8$ and $R_9$ are independently selected from the group consisting of hydrogen, lower alkyl ($C_1$-$C_4$), trifluoromethyl, cyano, halogen, hydroxy, nitro, lower alkoxy ($C_1$-$C_4$), amino or lower alkylamino; and $R_{10}$ represents aryl which may be substituted with one or more substituents.

In accordance with a second aspect of the present invention there is provided a compound having the structure of Formula II and its pharmaceutically acceptable salts, pharmaceutically acceptable solvates, esters, enantiomers, diastereomers, N-oxides, polymorphs, metabolites, wherein W, X, Y, Z, Q, $R_7$, $R_8$, $R_9$ and $R_{10}$ are as defined for Formula I.

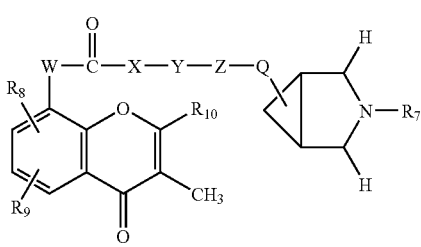

Formula II (Formula I, wherein $R_5 = R_6 = H$)

In accordance with a third aspect of the present invention, there is provided a method for treatment or prophylaxis of an animal or a human suffering from a disease or disorder of the respiratory, urinary and gastrointestinal systems, wherein the disease or disorder is mediated through muscarinic receptors, comprising administering to a patient in need thereof, an effective amount of compounds as described above.

In accordance with a fourth aspect of the present invention, there is provided a method for treatment or prophylaxis of an animal or a human suffering from a disease or disorder associated with muscarinic receptors, comprising administering to a patient in need thereof, an effective amount of compounds as described above.

In accordance with a fifth aspect of the present invention, there is provided a method for treatment or prophylaxis of an animal or a human suffering from a disease or disorder of the respiratory systems such as bronchial asthma, chronic obstructive pulmonary disorders (COPD), pulmonary fibrosis, etc., urinary system which induce such urinary disorders as urinary incontinence, lower urinary tract systems (LUTS), etc., and gastrointestinal system such as irritable bowel syndrome, obesity, diabetes and gastrointestinal hyperkinesis with compound as described above, wherein the disease or disorder is associated with muscarinic receptors, comprising administering to a patient in need thereof, an effective amount of compounds as described above.

In accordance with a sixth aspect of the present invention, there is provided a process for preparing the compounds as described above.

The compounds of the present invention exhibit significant potency in terms of their activity, which was determined by in vitro receptor binding and functional assays and in vivo experiments using anaesthetised rabbit. Compounds were tested in vitro and in vivo. Some compounds were found to function as potent muscarinic receptor antagonists with high affinity towards $M_3$ receptors. Therefore, the present invention provides pharmaceutical compositions for treatment of diseases or disorders associated with muscarinic receptors. Compounds and compositions described herein can be administered orally or parenterally.

DETAILED DESCRIPTION OF THE INVENTION

The compounds described herein may be prepared by techniques well known in the art and familiar to the average synthetic organic chemist. In addition, the compounds described herein may be prepared by the following reaction sequence:

Scheme-I

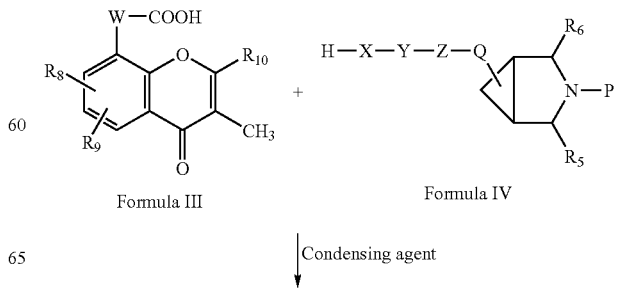

Formula III      Formula IV

Condensing agent

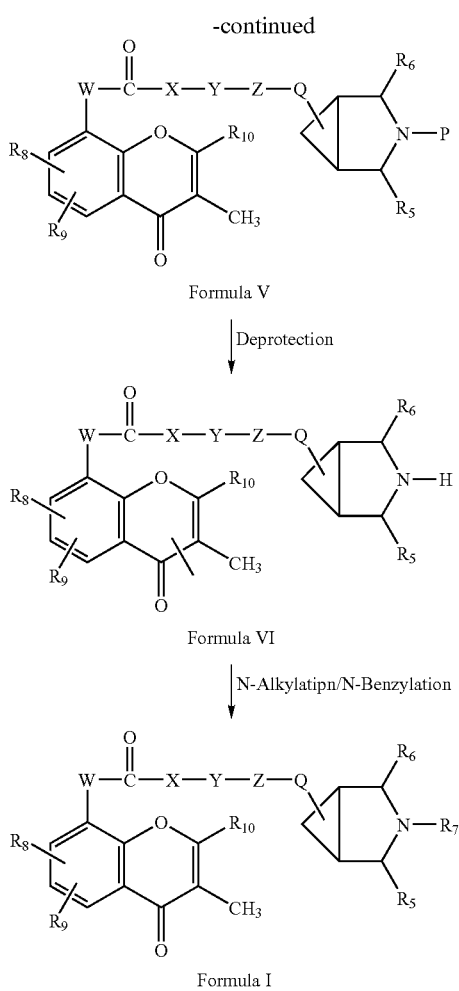

Formula V

Deprotection

Formula VI

N-Alkylatipn/N-Benzylation

Formula I

The compounds of Formula I of the present invention may be prepared by the reaction sequence as shown in Scheme I. The preparation comprises condensing a compound of Formula III with the compound of Formula IV wherein W represents $(CH_2)_p$, where p represents 0 to 1;

X represents an oxygen, sulphur, —NR or no atom, wherin R represents hydrogen or $C_{1-6}$ alkyl;

Y represents $CHR_1CO$, wherein $R_1$ represents hydrogen, methyl or $(CH_2)q$ wherein q represents 0 to 4;

Z represents oxygen, sulphur, $NR_2$, wherein $R_2$ represents hydrogen, or $C_{1-6}$alkyl;

Q represents $(CH_2)_n$, wherein n represents 0 to 4, or $CHR_3$ wherein $R_3$ represents H, OH, $C_{1-6}$ alkyl, $C_{1-6}$ alkenyl, $C_{1-6}$ alkoxy or $CH_2CHR_4$ wherein $R_4$ represents H, OH, lower alkyl $(C_1-C_4)$ or lower alkoxy $(C_1-C_4)$;

$R_5$ and $R_6$ are independently selected from H, COOH, $CH_3$, $CONH_2$, $NH_2$, $CH_2NH_2$;

$R_8$ and $R_9$ are independently selected from hydrogen, lower alkyl $(C_1-C_4)$, trifluoromethyl, cyano, hydroxy, nitro, lower alkoxy $(C_1-C_4)$, amino or lower alkylamino; and P is any group which can be used to protect an amino group in the presence of a condensing agent to give a protected compound of Formula V, which on deprotection through reaction with deprotecting agent in an organic solvent gives an unprotected compound of Formula VI which is finally N-alkylated or benzylated with a suitable alkylating or benzylating agent L-$R_7$ to give a compound of Formula I, wherein L is any leaving group and $R_7$ represents hydrogen, $C_1$-$C_{15}$ saturated or unsaturated aliphatic hydrocarbon groups in which any 1 to 6 hydrogen atoms may be substituted with the group independently selected from halogen, arylalkyl, arylalkenyl, heteroarylalkyl or heteroarylalkenyl having 1 to 2 hetero atoms selected from the group consisting of nitrogen, oxygen and sulphur atoms with an option that any 1 to 3 hydrogen atoms on an aryl or heteroaryl ring in said arylalkyl, arylalkenyl, hetero arylalkenyl group may be substituted with lower alkyl $(C_1-C_4)$, lower perhalo alkyl $(C_1-C_4)$, cyano, hydroxyl, nitro, lower alkoxycarbonyl, halogen, lower alkoxy $(C_1-C_4)$, lower perhaloalkoxy $(C_1-C_4)$, unsubstituted amino, N-lower alkylamino $(C_1-C_4)$, N-lower alkylamino carbonyl $(C_1-C_4)$, N,N-lower dialkylamino $(C_1-C_4)$, N,N-lower dialkylaminocarboynl.

P is any protecting group for an amino group for a compound of Formula VI and is selected from benzyl and t-butyloxy carbonyl groups.

The reaction of the compound of Formula III with a compound of Formula IV to give a compound of Formula V can be carried out in the presence of a condensing agent, for example 1-(3-dimethylaminopropyl)-3-ethyl carbodiimide hydrochloride (EDC) and 1,8-diazabicyclo[5.4.0]undec-7ene (DBU).

The reaction of the compound of Formula III with a compound of Formula IV to give a compound of Formula V can be carried out in a suitable solvent, for example, N, N-dimethylformamide, dimethylsulfoxide, toluene and xylene at a temperature ranging from about 0 to about 140° C.

The deprotection of the compound of Formula V to give a compound of Formula VI can be carried out with a deprotecting agent, for example, palladium on carbon, trifluoroacetic acid (TFA) and hydrochloric acid.

The deprotection of the compound of Formula V to give a compound of Formula VI can be carried out in a suitable organic solvent, for example those selected from the group consisting of methanol, ethanol, tetrahydrofuran and acetonitrile at temperatures ranging from about 10 to about 50° C.

The N-alkylation or benzylation of the compound of Formula VI to give a compound of Formula I can be carried out with a suitable alkylating or benzylating agent, L-$R_7$ wherein L is any leaving group, known in the art, for example, halogen, O-mestyl and O-tosyl group.

The N-alkylation or benzylation of the compound of Formula VI to give a compound of Formula I can be carried out in a suitable organic solvent such as N,N-dimethylformamide, dimethylsulfoxide, tetrahydrofuran and acetonitrile at temperature ranging from about 25 to about 100° C.

In the above scheme, where specific bases, condensing agents, protecting groups, deprotecting agents, N-alkylating/benzylating agents, solvents, etc. are mentioned, it is to be understood that other bases, condensing agents, protecting groups, deprotecting agents, N-alkylating/benzylating agents, solvents, etc. known to those skilled in the art may be used. Similarly, the reaction temperature and duration may be adjusted according to the desired needs.

Suitable salts of compounds represented by the Formula I were prepared so as to solubilize the compound in aqueous medium for biological evaluations. Examples of such salts are pharmacologically acceptable salts such as inorganic acid salts (e.g. hydrochloride, hydrobromide, sulphate, nitrate and phosphrate), organic acid salts (e.g. acetate, tartarate, citrate, fumarate, maleate, tolounesulphonate and methanesulphonate). When a carboxyl group is included in the Formula I as a substituent, it may be in its alkali metal salt form (e.g. sodium, potassium, calcium, magnesium, and the like). These salts may be prepared by usual prior art techniques, such as treating the compound with an equivalent amount of inorganic or organic, acid or base in a suitable solvent.

Particular compounds which are capable of being produced by Scheme I include:

Compound No. Chemical Name (1α,5α,6α)-6N-[3-benzyl-3-azabicyclo[3.1.0]hexyl]-3-methyl-4-oxo-α-phenyl-4H-1-benzopyran-8-carboxamide (Compound No. 1)

(1α,5α,6α)-6N-[3-(4-cyanobenzyl)-3-azabicyclo[3.1.0] hexyl]-3-methyl-4-oxo-2-phenyl-4H-1-benzopyran-8-carboxamide (Compound No.2)

(1α,5α,6α)-N-[3-benzyl-3-azabicyclo[3.1.0]hexyl-6-(aminomethyl)-yl]-3-methyl-4-oxo-2-phenyl-4H-1-benzopyran-8-carboxamide (Compound No. 3)

(1α,5α,6α)-N-[3-(4-methyl-3-pentyl)-3-azabicyclo[3.1.0] hexyl-6-(aminomethyl)-yl]-3-methyl-4-oxo-2-phenyl-4H-1-benzopyran-8-carboxamide (Compound No. 4)

N-[3-benzyl-3-azabicyclo[3.1.0]hexyl-1-(aminomethyl)-yl]-3-methyl-4-oxo-2-phenyl-4H-1-benzopyran-8-carboxamide (Compound No. 5)

Compounds or compositions disclosed herein may be administered to an animal for treatment orally, or by a parenteral route. Pharmaceutical compositions disclosed here can be produced and administered in dosage units, each unit containing a certain amount of at least one compound described herein and/or at least one physiologically acceptable salt addition thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The present invention also includes the enantiomers, diastereomers, N-Oxides, polymorphs, solvates and pharmaceutically acceptable salts of these compounds as well as metabolites having the same type of activity. The present invention further includes pharmaceutical composition comprising the molecules of Formula I and II, or prodrugs, metabolites, enantiomers, diastereomers, N-oxides, polymorphs, solvates or pharmaceutically acceptable salts thereof, in combination with pharmaceutically acceptable carrier and optionally included excipients.

The examples mentioned below demonstrate the general synthetic procedure as well as the specific preparation of the preferred compound. The examples are provided to illustrate the particular aspects of the disclosure and should not be constrained to limit the scope of the present invention, as defined by the claims.

EXAMPLES

Various solvents, such as acetone, methanol, pyridine, ether, tetrahydrofuran, hexanes, and dichloromethane were dried using various drying reagents according to the procedures well known in the literature. 1R spectra were recorded as nujol mulls or a thin neat film on a Perkin Elmer Paragon instrument, Nuclear Magnetic Resonance (NMR) spectra were recorded on a Varian XL-300 MHz instrument using tetramethylsilane as an internal standard.

Example 1

Synthesis of (1α,5α,6α)-6N-[3-benzyl-3-azabicyclo [3.1.0]hexyl]-3methyl-4-oxo-2-phenyl-4H-1-benzopyran-8-carboxamide (Compound No. 1)

Step a: Synthesis of Monoprotected (1α,5α,6α)-6-amino-3-azabicyclo[3.1.0]hexane

The compound monoprotected (1α,5α,6α)-6-amino-3-azabicyclo[3.1.0]hexane was synthesized following the procedure of T. F. Braish et al., Synlett, 1996, 1100.

Step b: Synthesis of (1α,5α,6α)-6N-[3-benzyl-3-azabicyclo [3.1.0]hexyl-3methyl-4-oxo-2-phenyl-4H-1-benzopyran-8-carboxamide A solution of flavone-8-carboxylic acid which was available commercially from Lancaster (1 mmol) and monoprotected (1α,5α,6α)-6-amino-3-azabicyclo[3.1.0]hexane (1.5 mmol) in DMF was cooled to 0° C. 1-Hydorxy benzotriazole (1.2 mmol) was added to the reaction mixture (RM) followed by the addition of N-methylmorpholine (1 mmol) and the reaction mixture was stirred for 30 minutes. 1-(3-dimethylaminopropyl)-3-ethyl carbodimide hydrochloride was added and the reaction mixture was stirred for 3 hrs at 0° C. followed by stirring at RT for overnight. The RM was poured into water and extracted with ethyl acetate. The organic layer was dried and the residue obtained after removal of solvents was used as such.

mp=182-184° C.,

IR(KBr): 3287, 2276, 1635 cm$^{-1}$, $^1$HNMR δ values: 8.48-8.45 (m, 1H), 8.37-8.35 (m, 1H), 7.65-7.63 (m, 5H), 7.58-7.57 (m, 1H), 7.32-7.22 (m, 5H), 3.58 (S, 2H), 3.33 (m, 1H), 3.12 (d, 2H, 5=9.0 Hz), 2.40 (d, 2H, J=9.0 Hz), 2.18 (s, 3H), 1.74 (bs, 1H), 1.43 (m, 2H);

Mass (m/z)=451.2.

Example 2

Synthesis of (1α,5α,6α)-6N-[3-(4-cyanobenzyl)-3-azabiayclo[3.1.0]hexyl]-3-methyl-4-oxo-2phenyl-4H-1-benzopyran-8-carboxamide (Compound No. 2)

Step a: The title compound of Example 1 was added to a suspension of 10% palladium on carbon in methanol and the RM stirred at room temperature for 10 hours under hydrogen atmosphere. The RM was filtered over celite. The residue obtained after removal of solvent was used as such in the next step.

Step b: Synthesis of (1α,5α,6α)-6N-[3-(4cynobenzyl)-3-azabicylo[3.1.0]hexyl]-3-methyl-4-oxo-2-phenyl-4H-1-benzopyran-8-carboxamide A solution of the compound prepared in step a (1 mmol), 4-cyano benzoylbromide (1.2 mmol), potassium carbonate (8 mmol) and potassium iodide (2 mmol) in DMF (10 ml) was stirred at room temperature for 48 hours. The RM was poured into water and extracted with ethyl acetate. The organic layer was dried and the residue obtained after removal of the solvent was purified by column chromatography (100-200 mesh silicagel), eluting the product with 70% ethyl acetate-hexane mixture.

m.p: 213-215° C.;

IR (KBr): 3281, 2221, 1639 cm$^-$;

$^1$HNMR δ values: 8.852-8.49 (m, 1H), 8.41-8.38 (m, 1H), 7.65-7.36(m, 10H), 3.62 (5, 2H), 3.31 (m, 1H) 3.11 (d, 2H, J=9.0 Hz), 2.40 (d, 2H, J=9 Hz), 2.29 (s, 3H), 1.44 (m, 2H); Mass(m/z)=476

Example 3

Synthesis of (1α,5α,6α)-N-[3-benzyl-3-azabicyclo [3.1.0]hexyl-6-(aminomethyl)-yl]-3-methyl-4-oxo-2-phenyl-4H-1-benzopyran-8-carboxamide (Compound No. 3)

Step a: Synthesis of Monoprocted (1α,5α,6α)-6-aminomethyl-3-benzyl-3-azabicyclo[3.1.0]hexane The compound monoprocted (1α,5α,6α)-6-aminomethyl-3-benzyl-3-azabicyclo[3.1.0]hexane was synthesised as per the procedure of EP 0413455A2.

Step b: Synthesis of Monoprotected (1α,5α,6α)-N-[3-benzyl]-3-azabicyclo[3.1.0]hexyl 6-amino methyl)-yl)-3methyl-4-oxo-2-phenyl-4H-1-benzo-8-carboxamide This compound was synthesized following the procedure as in Example 1, step-b using (1α,5α,6α)-6-aminomethyl-3-benzyl-3-azabicyclo[3.1.0]hexane instead of (1α,5α, 6α)-6-amino-3-azabicyclo[3.1.0]hexane. The compound was purified by column chromatography 100-200 mesh size silicagel), eluting the compound with 70% ethyl acetate-hexane mixture.

m.p=175-177° C.
IR(KBr): 3293, 2921, 1645 cm$^{-1}$,
$^1$H NMR δ values: 8.852-8.559 (m, 1H), 8.41-8.44 (m, 1H), 7.53-7.70 (m, 6H), 5.12 (m, 1H), 3.17-3.25 (m, 3H), 2.36-2.43 (m, 4H), 2.23 (s, 3H), 2.12-2.17 (m, 2H), 1.61-1.71 (m, 6H), 1.45 (m, 2H)
Mass m/z=443.2

Example 4

Synthesis of (1α,5α,6α)-N-[3-[4-methyl-3-pentenyl]-3-azabicylo[3.1.0]hexyl-6-(aminomethyl)-3-methyl-4-oxo-2-phenyl-4H-1-benzo-pyran-8-carboxamide (Compound No 4)

Step a: Synthesis of (1α,5α,6α)-N-[3-azabicyclo[3.1.0]hexyl-6-(aminomethyl)-yl]-3-methyl-4-oxo-2-phenyl-4H-benzo-8-carboxamide The compound (1α,5α,6α)-N-[3-benzyl-3-azabicyclo[3.1.0]hexyl-6-(aminomethyl)-yl]-3-methyl-4-oxo-2-phenyl-4H-1-benzopyran-8-carboxamide was added to a suspension of 10% Pd-C in methanol and the reaction mixture was stirred at room temperature for 10 hr under hydrogen atmosphere. The reaction mixture was filtered over celite pad. The residue obtained after the removal of solvents was used as such in the next step.

Step b: Synthesis of (1α,5α,6α)-6N-[3-(4methyl-3-pentenyl)-3-azabicyclo[3.1.0]hexyl]-3-methyl-4-oxo-2-phenyl-4H-1-benzopyran-8-carboxamide A solution of the compound prepared in step a (1 mmol), 4-methyl-3-pentenoyl bromide (1.2 mmol), potassium carbonate (8 mmol) and potassium iodide (2 mmol) in DMF (10 ml) was stirred at room temperature for 48 hours. The reaction mixture was poured into water and extracted with ethyl acetate. The organic layer was dried and the residue obtained after removal of the solvent was purified by column chromatography (100-200 mesh silicagel), eluting the product with 70% ethyl acetate-hexane mixture.

m.p: 125-127° C.;
IR (KBr): 3310, 2832, 1641 cm$^{-1}$;
$^1$HNMR δ values: 8.41-8.38 (m, 1H), 8.35-8.32 (m, 1H), 7.66-7.64 (m, 2H), 7.54-7.43 (m, 4H), 7.31-7.25 (m, 5H), 3.54 (5, 2H), 3.30-3.26 (m, 2H), 2.74 (d, 2H, J=9 Hz), 2.24-2.17 (m, 5H), 1.41 (bs, 1H), 1.19 (m, 2H);
Mass m/z=(465.1)

Example 5

Synthesis of N-[3-benzyl-3-azabicyclo[3.1.0]hexyl-1-(amino methyl)-yl]-3-methyl-4-oxo-2-phenyl-4H-1-benzo-8-caboxamide. (Compound No.5)

Step a: Synthesis of 1-aminomethyl-3-benzyl-3-azabicyclo[3.1.0]hexane
The compound was synthesized following the procedure described in EP 0413 4 55A2

Step b: Synthesis of N-[3-benzyl-3-azabicylo[3.1.0]hexyl-1-(aminomethyl)-3-methyl-4-oxo-2-phenyl-4H-1-benzo-8-carboxamide A solution of flavone-8-caboxylic acid (1 mmol) which was available commercially from Lancaster and monoprotected (1α,5α,6α)-6-amino-3-azabicyclo[3.1.0]hexane which was synthesized following the procedure of T. F. Braish et al., Synlett, 1996, 1100. (1.5 mmol) in dimethylformamide was cooled to 0° C. 1-hydroxy benzotriazole (1.2 mmol) followed by N-methyl morpholine (1 mmol) was added to the reaction mixture and stirred for 30 minutes. 1-(3-dimethylaminopropyl)-3-ethyl-carbodiimide hydrochloride was added and the reaction mixture was stirred for 3 hr. at 0° C. followed by stirring at room temperature for overnight. The reaction mixture was poured into water and extracted with ethyl acetate. The organic layer was dried and the semisolid obtained after the removal of the solvent was used as such.

IR (KBr): 3445, 2788, 1636 cm$^{-1}$;
$^1$H(NMR): 8.42-8.54 (m, 2H), 7.49-7.63 (m, 6H), 7.22-7.32 (m, 5H), 3.76 (m, 1H), 3.49 (s, 2H), 3.35-3.37 (m, 1H), 2.82-2.85 (m, 1H), 2.72-2.75 (m, 1H) 2.16-2.25 (m, 5H), 1.12-1.26 (m, 1H), 0.89-0.91 (m, 1H), 0.27-0.29 (m, 1H);
Mass (m/z)=465.2.

Example 6

Biological Activity

Radioligand Binding Assays:

The affinity of test compounds for $M_2$ and $M_3$ muscarinic receptor subtypes was determined by [$^3$H]-N-methylscopolamine binding studies using rat heart and submandibular gland respectively as described by Moriya et al., (Life Sci, 1999, 64(25):2351-2358) with minor modifications.

Membrane preparation: Submandibular glands and heart were isolated and placed in ice cold homogenising buffer (HEPES 20 mM, 10 mM EDTA, pH 7.4) immediately after sacrifice. The tissues were homogenised in 10 volumes of homogenising buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at –70° C. until the time of assay.

Ligand binding assay: The compounds were dissolved and diluted in DMSO. The membrane homogenates (150-250 µg protein) were incubated in 250 µl of assay buffer (HEPES 20 mM, pH 7.4) at 24-25° C. for 3 h. Non-specific binding was determined in the presence of 1 µM atropine. The incubation was terminated by vacuum filtration over GF/B fiber filters (Wallac). The filters were then washed with ice cold 50 mM Tris HCl buffer (pH 7.4). The filter mats were dried and bound radioactivity retained on filters was counted. The $IC_{50}$ & Kd were estimated by using the non-linear curve fitting program using G Pad Prism software. The value of inhibition constant Ki was calculated from competitive binding studies by using Cheng & Prusoff equation (*Biochem Pharmacol*, 1973, 22: 3099-3108), Ki=$IC_{50}$/(1+L/Kd), where L is the concentration of [³H]NMS used in the particular experiment. pki is—[log Ki].

The results of the in-vitro tests are listed in Tables I.

TABLE I

|  | Receptor Binding Assay | |
| --- | --- | --- |
|  | $M_2$ pki | $M_3$ pki |
| Compound No. 1 | <5 | <5 |
| Compound No. 2 | <5 | <5 |
| Compound No. 3 | <5.3 | 5.1 |
| Compound No. 4 | <6 | <6 |
| Compound No. 5 | <6 | <6 |
| Tolterodine | 8.3 | 8.13 |

While the present invention has been described in terms of its specific embodiments, certain modifications and equivalents will be apparent to those skilled in the art and are intended to be included within the scope of the present invention.

What is claimed is:

1. A compound selected from the group consisting of:
   (1α, 5α, 6α)-6N-[3-benzyl-3-azabicyclo[3.1.0]hexyl]-3-methyl-4-oxo-α-phenyl-4H-1-benzopyran-8-carboxamide (Compound No. 1);
   (1α, 5α, 6α)-6N-[3-(4-cyanobenzyl)-3-azabicyclo[3.1.0]hexyl]-3-methyl-4-oxo-2-phenyl-4H-1-benzopyran-8-carboxamide (Compound No. 2);
   (1α,5α, 6α)-N-[3-benzyl-3-azabicyclo [3.1.0]hexyl-6-(aminomethyl)-yl]-3-methyl-4-oxo-2-phenyl-4H-1-benzopyran-8-carboxamide (Compound No. 3);
   (1α,5α,6α)-N-[3-(4-methyl-3-pentyl)-3-azabicyclo[3.1.0]hexyl-6-(aminomethyl)-yl]-3-methyl-4-oxo-2-phenyl-4H-1-benzopyran-8-carboxamide (Compound No. 4); and
   N-[3-benzyl-3-azabicyclo[3.1.0]hexyl-1-(aminomethyl)-yl]-3-methyl-4-oxo-2-phenyl-4H-1-benzopyran-8-carboxamide (Compound No. 5).

2. A pharmaceutical composition comprising a pharmaceutically effective amount of a compound as defined in claim 1 together with pharmaceutically acceptable carriers, excipients, or diluents.

3. A method for treatment of an animal or a human suffering from a disease or disorder of the respiratory, urinary and gastrointestinal systems, wherein the disease or disorder is urinary incontinence, bronchial asthma, chronic obstructive pulmonary disorders (COPD), pulmonary fibrosis, irritable bowel syndrome, obesity, diabetes, and gastrointestinal hyperkinesis, comprising administering to said animal or human, a therapeutically effective amount of a compound of claim 1.

4. The method for treatment of an animal. or a human suffering from a disease or disorder of the respiratory, urinary, and gastrointestinal systems, wherein the disease or disorder is urinary incontinence, bronchial asthma, chronic obstructive pulmonary disorders (COPD), pulmonary fibrosis, irritable bowel syndrome, obesity, diabetes, and gastrointestinal hyperkinesis, comprising administering to said animal or human, a therapeutically effective amount of the pharmaceutical composition according to claim 2.

* * * * *